US010428046B2

(12) United States Patent
Yamamoto et al.

(10) Patent No.: US 10,428,046 B2
(45) Date of Patent: Oct. 1, 2019

(54) N-SUBSTITUTED SULFONAMIDE COMPOUND AND METHOD FOR PRODUCING SAME

(71) Applicant: UBE INDUSTRIES, LTD., Ube-shi, Yamaguchi (JP)

(72) Inventors: Yasuhito Yamamoto, Ube (JP); Masayoshi Oue, Ube (JP); Yukinori Wada, Ube (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 0 days.

(21) Appl. No.: 15/317,817

(22) PCT Filed: Jun. 10, 2015

(86) PCT No.: PCT/JP2015/066689
§ 371 (c)(1),
(2) Date: Dec. 9, 2016

(87) PCT Pub. No.: WO2015/190507
PCT Pub. Date: Dec. 17, 2015

(65) Prior Publication Data
US 2017/0114043 A1 Apr. 27, 2017

(30) Foreign Application Priority Data

Jun. 10, 2014 (JP) ................. 2014-119691

(51) Int. Cl.
*C07D 401/14* (2006.01)
*C07D 213/74* (2006.01)

(52) U.S. Cl.
CPC ......... *C07D 401/14* (2013.01); *C07D 213/74* (2013.01)

(58) Field of Classification Search
CPC .................................................. C07D 401/14
See application file for complete search history.

(56) References Cited

U.S. PATENT DOCUMENTS

| 2005/0171180 A1 | 8/2005 | Resnick et al. |
| 2007/0203245 A1 | 8/2007 | Koltun et al. |
| 2008/0214394 A1 | 9/2008 | Puhl et al. |
| 2010/0273739 A1 | 10/2010 | Amberg et al. |
| 2011/0054172 A1 | 3/2011 | Iwamura et al. |
| 2012/0190852 A1 | 7/2012 | Hagihara et al. |
| 2013/0184238 A1 | 7/2013 | Amberg et al. |
| 2014/0031331 A1 | 1/2014 | Amberg et al. |
| 2014/0113907 A1 | 4/2014 | Iwamura et al. |
| 2016/0060221 A1 | 3/2016 | Shibakawa et al. |

FOREIGN PATENT DOCUMENTS

| CA | 2757291 | * 10/2010 | |
| CN | 102911086 A | 2/2013 | |
| JP | 2002-322054 A | 11/2002 | |
| JP | 2011-57633 A | 3/2011 | |
| WO | WO 2007/067817 A1 | 6/2007 | |
| WO | WO 2008/103615 A1 | 8/2008 | |
| WO | WO 2009/086123 A1 | 7/2009 | |
| WO | WO 2009/113600 A1 | 9/2009 | |
| WO | WO 2010/059627 A1 | 5/2010 | |
| WO | WO 2010/113957 A1 | 10/2010 | |
| WO | WO 2010/125831 A1 | 11/2010 | |
| WO | WO 2011/011722 A1 | 1/2011 | |
| WO | WO 2011/028741 A1 | 3/2011 | |
| WO | WO 2011/030865 A1 | 3/2011 | |
| WO | WO 2011030865 | * 3/2011 | ........... C07D 213/74 |
| WO | WO 2014/157672 A1 | 10/2014 | |
| WO | WO 2016/047742 A1 | 3/2016 | |

OTHER PUBLICATIONS

Chmielewski. Heterocycles, 1987, 25, 533-40. (Year: 1987).*
U.S. Appl. No. 15/317,875, filed Dec. 9, 2016.
Brettle et al., "N-Alkylation of some Secondary Styryl Enamides", J. Chem. Soc. Perkin Trans. I, 1985, pp. 831-836.
Cardullo et al., "Parallel Protocol for the Selective Methylation and Alkylation of Primary Amines", J. Comb. Chem., 2006, vol. 8, pp. 834-840.
Chernyshev et al., "Alkylation of Acyl and Sulfonyl Derivatives of 3,5-Diamino-1-Phenyl-1,2,4-Triazole", Chemistry of Heterocyclic Compounds, 2009, vol. 45, No. 4, pp. 436-444.
Cirauqui et al., "New Amide Derivatives as Melanin-concentrating Hormone Receptor 1 Antagonists for the Treatment of Obesity", Arzneimittel-Forschung (Drug Research), 2008, vol. 58, No. 11, pp. 585-591.
Hu et al., "2,4-Thiazolidinediones as Potent and Selective Human $\beta_3$ Agonists", Bioorganic & Medicinal Chemistry Letters, 2011, vol. 11, pp. 757-760.
Inoue et al., "Boron-Mediated Aldol Reaction of Carboxylic Esters: Complementary Anti- and Syn-Selective Asymmetric Aldol Reactions", J. Org. Chem., 2002, vol. 67, pp. 5250-5256.
International Search Report, issued in PCT/JP2015/066689, dated Jul. 14, 2015.
MacPherson et al., "Discovery of CGS 27023A, a Non-Peptidic, Potent, and Orally Active Stromelysin Inhibitor That Blocks Cartilage Degradation in Rabbits", J. Med. Chem., 1997, vol. 40, pp. 2525-2532.
Shono et al., "Electrooxidative Rearrangement of Tosylamino Group: Facile Synthesis of α-Amino Aldehydes From Primary Amines", Tetrahedron Letters, 1986, vol. 27, No. 50, pp. 6083-6086.
Effenberger et al., "Darstellung und Reaktionen von Trifluormethansulfonsäure-sulfonsäure-anhydriden," Angewandte Chemie, vol. 86, No. 11, XP002773659, Jan. 1974, pp. 409-410.
Extended European Search Report for European Application No. 15806408.9, dated Oct. 23, 2017.

(Continued)

*Primary Examiner* — Noble E Jarrell
(74) *Attorney, Agent, or Firm* — Birch, Stewart, Kolasch & Birch, LLP

(57) ABSTRACT

The present invention relates to a method for producing N-substituted sulfonamide compounds including a step of reacting a sulfonamide compound of general formula (1) with a halogenated organic compound of general formula (2) in the presence of cesium carbonate or potassium carbonate in an organic solvent to produce an N-substituted sulfonamide compound of general formula (3).

15 Claims, No Drawings

(56) References Cited

OTHER PUBLICATIONS

Barton et al., "Discovery and optimisation of a potent and selective tertiary sulfonamide oxytocin antagonist," Bioorganic & Medicinal Chemistry Letters, vol. 19, 2009 (available online Nov. 12, 2008), XP025816981, pp. 528-532.

Extended European Search Report issued in European Application No. 15807453.4 dated Jan. 2, 2018.

Fletcher et al., "Structure-Based Design and Synthesis of Potent, Ethylenediamine-Based, Mammalian Farnesyltransferase Inhibitors as Anticancer Agents," Journal of Medicinal Chemistry, vol. 53, No. 19, 2010 (published on Web Sep. 7, 2010), XP055435372, pp. 6867-6888.

Sexton et al., "Inhibitors of Lipoprotein(a) Assembly," Bioorganic & Medicinal Chemistry, vol. 11, 2003, XP001181005, pp. 4827-4845.

Bonk et al., "Convenient One-Pot Synthesis of Sulfonamides from Thiols using Trichloroisocyanuric Acid," Synthetic Communications, vol. 37, No. 12, 2007, pp. 2039-2050 (Total 13 pages).

File registry on STN, RN 51567-94-3, Entered STN: Nov. 16, 1984, 1 page.

International Search Report and Written Opinion of the International Searching Authority (forms PCT/ISA/210 and PCT/ISA/237), dated Jul. 14, 2015, for International Application No. PCT/JP2015/066688, with an English translation of the International Search Report.

Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," Bioorganic & Medicinal Chemistry, vol. 6, 1998, pp. 673-686.

Morisawa et al., "Studies on Anticoccidial Agents. 13. Synthesis and Anticoccidial Activity of Nitropyridine-2-and-3-sulfonamides and Derivatives," Journal of Medicinal Chemistry, vol. 23, No. 12, 1980, pp. 1376-1380.

Shaabani et al., "A Novel Approach for the Synthesis of Alkyl and Aryl Sulfonamides," Tetrahedron Letters, vol. 48, 2007 (Available online Jan. 23, 2007), pp. 2185-2188.

Wright et al., "A Convenient Preparation of Heteroaryl Sulfonamides and Sulfonyl Fluorides from Heteroaryl Thiols," Journal of Organic Chemistry, vol. 71, No. 3, 2006 (Published on web Jan. 11, 2006), pp. 1080-1084.

Chinese Office Action and Search Report, dated Mar. 6, 2019, for Chinese Application No. 201580031028.4, as well as an English translation of the Chinese Office Action.

Caddick et al., "Direct Synthesis of Sulfonamides and Activated Sulfonate Esters from Sulfonic Acids," J. Am. Chem. Soc., vol. 126, No. 4, 2004 (Published on Web Jan. 13, 2004), pp. 1024-1025.

\* cited by examiner

N-SUBSTITUTED SULFONAMIDE COMPOUND AND METHOD FOR PRODUCING SAME

TECHNICAL FIELD

The present invention relates to a method for producing an N-substituted sulfonamide compound with high purity by reacting a sulfonamide compound with a halogenated organic compound. The method for producing N-substituted sulfonamide compounds of the present invention involves a specific base, and thereby allows the reaction to proceed faster than heretofore possible and affords high yield with little byproducts, which makes the method of great usefulness in industry. Further, N-substituted sulfonamide compounds obtained by the production method of the present invention are useful as intermediates and active ingredients for drugs.

BACKGROUND ART

N-substituted sulfonamide compounds are useful in various fields as medicinal and agrochemical products and organic materials, or as raw materials and intermediates thereof. In particular, they have recently been reported to be useful as medicinal products. Safe and convenient methods for their production have been desired (for example, see Patent Documents 1 and 2).

In some methods presented so far, N-substituted sulfonamide compounds are produced by reacting a sulfonamide compound with a halogenated organic compound in the presence of sodium hydride (for example, see Patent Documents 1 and 2, and Non-Patent Documents 1 to 5).

In other methods, N-substituted sulfonamide compounds are produced by reacting a sulfonamide compound with a halogenated organic compound in the presence of potassium carbonate (for example, see Patent Documents 3 and 4, and Non-Patent Document 6).

Further, methods have been presented which produce an N-substituted sulfonamide compound by reacting a sulfonamide compound with a halogenated organic compound in the presence of sodium methoxide (for example, see Non-Patent Document 7).

CITATION LIST

Patent Documents

Patent Document 1: WO 2009/086123
Patent Document 2: WO 2010/059627
Patent Document 3: WO 2007/067817
Patent Document 4: Japanese Patent Application Publication No. 2011-057633

Non-Patent Documents

Non-Patent Document 1: Bioorganic & Medicinal Chemistry Letters, 2001, Vol. 11, 757-760
Non-Patent Document 2: Tetrahedron Letters, 1986, Vol. 27, No. 50, 6083-6086
Non-Patent Document 3: J. Med. Chem., 1997, Vol. 40, 2525-2532
Non-Patent Document 4: J. Chem. Soc. Perkin Trans. 1, 1985, 831-836
Non-Patent Document 5: J. Org. Chem., 2002, Vol. 67, 5250-5256
Non-Patent Document 6: Arzneimittel Forschung (Drug Research), 2008, Vol. 58, No. 11, 585-591
Non-Patent Document 7: Chemistry of Heterocyclic Compounds, 2009, Vol. 45, No. 4, 436-444

SUMMARY OF THE INVENTION

Problem to be Solved by the Invention

Sodium hydride used in reactions similar to those described above generates explosive hydrogen during the reaction, and bubbles vigorously and produces extreme heat to make controlling of the reaction temperature difficult. In addition to being very dangerous in reactions, sodium hydride has many safety problems when it is handled or disposed of, such as the generation of bubbles or heat. Further, sodium hydride is a strong base and acts on (reactive) functional groups of compounds having a complicated structure such as medicinal products, possibly giving rise to the occurrence of side reactions and consequent undesired impurities. Furthermore, sodium hydride is sold as a 60% oil dispersion (a mixture in mineral oil) which entails troublesome pretreatments such as the removal of oil. Thus, the production methods using sodium hydride are less attractive in industry.

The other methods are also not satisfactory in terms of yield and are less attractive in industry because of the risk that byproducts may be formed by the reaction of the base with reactive functional groups such as esters.

In general, medicinal products have a risk of unexpected side effects caused by trace impurities. To attain high quality of medicinal products, the synthesis thereof strongly demands an efficient production method that has high selectivity and does not have any impurities such as unreacted raw materials and byproducts. In particular, the poorness in selectivity and yield in near final stages of the production increases the risk that a large amount of impurities will remain, and therefore has a significant influence on the purity of pharmaceutical ingredients. Thus, there has been a strong demand for a safe, highly selective, and industrially advantageous method capable of producing N-substituted sulfonamides with high purity.

It is therefore an object of the present invention to provide a simple and industrially advantageous method which can produce N-substituted sulfonamide compounds with high yield and high purity. Another object is to provide an N-substituted sulfonamide compound having higher quality than before by such the production method.

Means for Solving the Problems

The present inventors carried out extensive studies on basic compounds used in the reaction between a sulfonamide compound and a halogenated organic compound. As a result, the present inventors have found that cesium carbonate or potassium carbonate allows the reaction to proceed quickly and with good selectivity, and have developed an industrially advantageous method for the production of high-purity N-sulfonamides which, by the use of such a base, can produce an N-substituted sulfonamide with high yield and high purity in a safe manner with little side reactions, thereby completing the present invention.

An aspect of the present invention resides in a method for producing N-substituted sulfonamide compounds including a step of reacting a sulfonamide compound of the general formula (1):

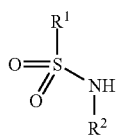

(1)

(wherein
$R^1$ and $R^2$ are each independently an optionally substituted alkyl, alkenyl, alkynyl, cycloalkyl, aryl, heteroaryl, aralkyl or heteroarylalkyl group) with a halogenated organic compound of the general formula (2):

$$R^3—X \qquad (2)$$

(wherein
$R^3$ is an optionally substituted alkyl, aralkyl or heteroarylalkyl group, and X is a halogen atom) in the presence of cesium carbonate or potassium carbonate in an organic solvent to produce an N-substituted sulfonamide compound of the general formula (3):

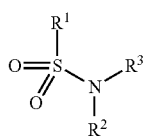

(3)

(wherein $R^1$, $R^2$ and $R^3$ are the same as defined above).

Effect of the Invention

According to the present invention, an N-substituted sulfonamide compound of the general formula (3) can be produced with high purity and in high yield selectively from a sulfonamide compound of the general formula (1) and a halogenated organic compound of the general formula (2) under mild conditions in a simple and industrially advantageous manner.

MODE FOR CARRYING OUT THE INVENTION

An N-substituted sulfonamide compound of the general formula (3) according to the present invention can be obtained by reacting a sulfonamide compound of the general formula (1) with a halogenated organic compound of the general formula (2) in the presence of cesium carbonate ($Cs_2CO_3$) or potassium carbonate ($K_2CO_3$) in an organic solvent (see [Reaction formula 1] below, which illustrates only the reaction using cesium carbonate).

[Reaction formula 1]

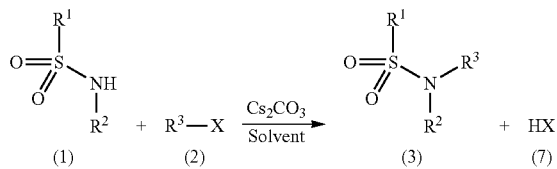

(In the formula, $R^1$, $R^2$, $R^3$ and X are the same as defined above.)

An N-substituted sulfonamide compound of the general formula (6) according to the present invention can be obtained by reacting a sulfonamide compound of the general formula (4) with a halogenated organic compound of the general formula (5) in the presence of cesium carbonate ($Cs_2CO_3$) or potassium carbonate ($K_2CO_3$) in an organic solvent (see [Reaction formula 1'] below, which illustrates only the reaction using cesium carbonate).

[Reaction formula 1']

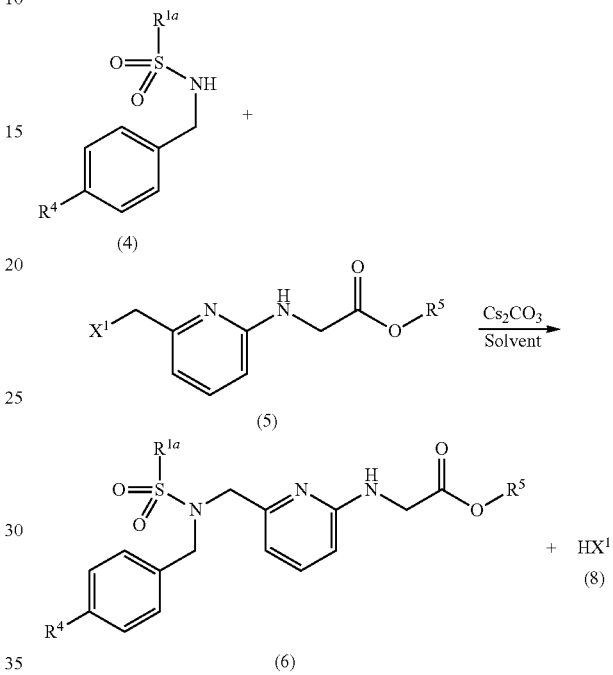

(In the formula, $R^{1a}$ is defined the same as $R^1$, $R^4$ is an optionally substituted aryl or heteroaryl group, $R^5$ is an alkyl group, and $X^1$ is defined the same as X.)

In the present invention, the following terms, alone or in combination with other terms, have the meanings given below, unless otherwise stated.

"Alkyl group" means a monovalent group of linear or branched, saturated aliphatic hydrocarbon. Typical examples include alkyl groups having 1 to 10 carbon atoms, for example, methyl group, ethyl group, propyl group, butyl group, pentyl group, hexyl group, heptyl group, octyl group, nonyl group and decyl group (including various isomers). Alkyl groups having 1 to 6 carbon atoms are preferable, with examples including methyl group, ethyl group, propyl group, isopropyl group, butyl group, isobutyl group and hexyl group. Alkyl groups having 1 to 4 carbon atoms are more preferable, with examples including methyl group, ethyl group, propyl group, isopropyl group, butyl group and isobutyl group.

"Alkenyl group" means a monovalent group of linear or branched, unsaturated aliphatic hydrocarbon which includes at least one carbon-carbon double bond. Typical examples include alkenyl groups having 2 to 10 carbon atoms, for example, vinyl group, propenyl group, butenyl group, pentenyl group, hexenyl group, heptenyl group, octenyl group, nonenyl group and decenyl group (including various isomers). Alkenyl groups having 2 to 6 carbon atoms are preferable, with examples including vinyl group, propenyl group, butenyl group, pentenyl group and hexenyl group. Alkenyl groups having 2 to 4 carbon atoms are more preferable, with examples including vinyl group, 1-propenyl group, 2-propenyl group, 1-butenyl group and 2-butenyl group.

"Alkynyl group" means a monovalent group of linear or branched, unsaturated aliphatic hydrocarbon which includes at least one carbon-carbon triple bond. Typical examples include alkynyl groups having 2 to 10 carbon atoms, for example, ethynyl group, propynyl group, butynyl group, pentynyl group, hexynyl group, heptynyl group, octynyl group, nonynyl group and decynyl group (including various isomers). Alkynyl groups having 2 to 6 carbon atoms are preferable, with examples including ethynyl group, propynyl group, butynyl group, pentynyl group and hexynyl group. Alkynyl groups having 2 to 4 carbon atoms are more preferable, with examples including ethynyl group, 2-propynyl group, 3-butynyl group and 2-butynyl group.

"Cycloalkyl group" means a monovalent group of cyclic saturated aliphatic hydrocarbon. Typical examples include cycloalkyl groups having 3 to 10 carbon atoms, for example, cyclopropyl group, cyclobutyl group, cyclopentyl group, cyclohexyl group, cycloheptyl group, cyclooctyl group, cyclononyl group and cyclodecyl group. Cycloalkyl groups having 3 to 8 carbon atoms are preferable, with examples including cyclopropyl group, cyclobutyl group, cyclopentyl group, cyclohexyl group, cycloheptyl group and cyclooctyl group. Cycloalkyl groups having 3 to 6 carbon atoms are more preferable, with examples including cyclopropyl group, cyclobutyl group, cyclopentyl group and cyclohexyl group.

"Aryl group" means a monovalent group of monocyclic or condensed polycyclic aromatic hydrocarbon. Typical examples include aryl groups having 6 to 14 carbon atoms, for example, phenyl group, naphthyl group and anthryl group. Aryl groups having 6 to 10 carbon atoms are preferable, with examples including phenyl group, 1-naphthyl group and 2-naphthyl group.

"Heteroaryl group" means a monovalent group of a monocyclic or condensed polycyclic aromatic heterocyclic compound which includes at least one hetero atom selected from the group consisting of a nitrogen atom, an oxygen atom and a sulfur atom. Typical examples include 5- to 10-membered heteroaryl groups, for example, pyrrolyl group, imidazolyl group, pyrazolyl group, triazolyl group, pyridyl group, pyrimidinyl group, pyridazinyl group, indolyl group, quinolyl group; thienyl group, benzothienyl group; furyl group, benzofuranyl group; oxazolyl group, isoxazolyl group, thiazolyl group, isothiazolyl group, oxadiazolyl group and thiadiazolyl group (including various isomers). 5- to 6-membered heteroaryl groups are preferable, with examples including 2-pyrrolyl group, 3-pyrrolyl group, 1-pyrazolyl group, 1,2,4-triazol-1-yl group, 2-pyridyl group, 3-pyridyl group, 4-pyridyl group, 2-pyrimidinyl group, 4-pyridazinyl group, 2-thienyl group, 3-thienyl group, 2-furyl group, 3-furyl group, 2-thiazolyl group and 4-thiazolyl group.

"Aralkyl group" means an alkyl group substituted with an aryl group. Here, "aryl group" and "alkyl group" are the same as defined above. Typical examples include aralkyl groups having 7 to 14 carbon atoms, for example, benzyl group, phenethyl group, phenylpropyl group, phenylbutyl group, naphthylmethyl group and naphthylethyl group (including various isomers). Aralkyl groups having 7 to 10 carbon atoms are preferable, with examples including benzyl group, 1-phenethyl group, 2-phenethyl group, 3-phenylpropyl group and 4-phenylbutyl group.

"Heteroarylalkyl group" means an alkyl group substituted with a heteroaryl group. Here, "heteroaryl group" and "alkyl group" are the same as defined above. Typical examples include 6- to 14-membered heteroarylalkyl groups, for example, pyrrolylmethyl group, pyrrolylethyl group, imidazolylmethyl group, imidazolylethyl group, pyrazolylmethyl group, pyrazolylethyl group, triazolylmethyl group, triazolylethyl group, pyridylmethyl group, pyridylethyl group, pyrimidinylmethyl group, pyrimidinylethyl group, pyridazinylmethyl group, pyridazinylethyl group, indolylmethyl group, indolylethyl group, quinolylmethyl group, quinolylmethylethyl group; thienylmethyl group, thienylethyl group, benzothienylmethyl group, benzothienylethyl group; furylmethyl group, furylethyl group, benzofuranylmethyl group, benzofuranylethyl group; oxazolylmethyl group, oxazolylethyl group, isoxazolylmethyl group, isoxazolylethyl group, thiazolylmethyl group, thiazolylethyl group, isothiazolylmethyl group, isothiazolylethyl group, oxadiazolylmethyl group, oxadiazolylethyl group, thiadiazolylmethyl group and thiadiazolylethyl group (including various isomers). 6- to 10-membered heteroarylalkyl groups are preferable, with examples including 2-pyridylmethyl group, 3-pyridylmethyl group, 2-pyrimidinylmethyl group, 5-pyrimidinylmethyl group, 2-indolylmethyl group, 5-indolylmethyl group, 2-benzofuranylmethyl group, 5-indolylmethyl group, 2-benzothienylmethyl group and 5-benzothienylmethyl group.

"Halogen atom" or "halo" means a fluorine atom, a chlorine atom, a bromine atom or an iodine atom, preferably a chlorine atom, a bromine atom or an iodine atom, and more preferably a chlorine atom or a bromine atom.

In the compounds of the general formulae (1) and (3), $R^1$ and $R^2$ are each independently an optionally substituted alkyl, alkenyl, alkynyl, cycloalkyl, aryl, heteroaryl, aralkyl or heteroarylalkyl group.

In the present invention, the phrase "optionally substituted" means, unless otherwise stated, that the group mentioned after the phrase has at least one substituent or has no substituents (that is, the group is unsubstituted). For example, an "optionally substituted alkyl group" means a "substituted alkyl mmmgroup" or an "unsubstituted alkyl group", wherein the "alkyl group" is the same as defined hereinabove. The substituents are not particularly limited as long as they are inactive in the production methods of the present invention and do not cause any chemical inconsistency in the structure.

Examples of the substituents in the "optionally substituted alkyl groups", the "optionally substituted alkenyl groups", the "optionally substituted alkynyl groups" and the "optionally substituted cycloalkyl groups" in $R^1$ and $R^2$ include halogen atoms; hydroxyl groups; alkoxy groups having 1 to 10 carbon atoms; optionally substituted amino groups; cyano groups; and nitro groups. Two or more of the substituents may be the same as or different from one another.

Examples of the substituents in the "optionally substituted aryl groups", the "optionally substituted heteroaryl groups", the "optionally substituted aralkyl groups" and the "optionally substituted heteroarylalkyl groups" in $R^1$ and $R^2$ include halogen atoms; alkyl groups having 1 to 10 carbon atoms; alkenyl groups having 2 to 10 carbon atoms; alkynyl groups having 2 to 10 carbon atoms; optionally substituted aryl groups; optionally substituted heteroaryl groups; optionally substituted aralkyl groups; optionally substituted heteroarylalkyl groups; alkoxy groups having 1 to 10 carbon atoms; alkoxyalkoxy groups having 2 to 20 carbon atoms; acyl groups having 2 to 11 carbon atoms; alkoxycarbonyl groups having 2 to 11 carbon atoms; alkoxycarbonylalkyl groups having 3 to 21 carbon atoms; alkoxycarbonylalkoxy groups having 3 to 21 carbon atoms; aryloxy groups having 6 to 14 carbon atoms; aralkyloxy groups having 7 to 14 carbon atoms; haloalkyl groups having 1 to 4 carbon atoms; optionally substituted amino groups; cyano groups; and nitro groups. Two or more of the substituents may be the same as or different from one another. Further, any two substituents which are bonded to adjacent ring atoms may form a ring together with such ring atoms.

Examples of the substituents in the "optionally substituted aryl groups", the "optionally substituted heteroaryl group", the "optionally substituted aralkyl groups" and the "optionally substituted heteroarylalkyl groups" in the examples of the substituents described above include halogen atoms; alkyl groups having 1 to 10 carbon atoms; alkenyl groups having 2 to 10 carbon atoms; alkynyl groups having 2 to 10 carbon atoms; alkoxy groups having 1 to 10 carbon atoms; haloalkyl groups having 1 to 4 carbon atoms; cyano groups; and nitro groups. Two or more of the substituents may be the same as or different from one another.

"Alkoxy group having 1 to 10 carbon atoms" in the present invention means a group —OR (wherein R is any of the alkyl groups having 1 to 10 carbon atoms described hereinabove). Examples of the alkoxy groups having 1 to 10 carbon atoms include methoxy group, ethoxy group, propoxy group, butoxy group, pentyloxy group, hexyloxy group, heptyloxy group, octyloxy group, nonyloxy group and decyloxy group (including various isomers). Alkoxy groups having 1 to 6 carbon atoms are preferable, with examples including methoxy group, ethoxy group, propyloxy group, isopropyloxy group, butyloxy group, isobutyloxy group and hexyloxy group. Alkoxy groups having 1 to 4 carbon atoms are more preferable, with examples including methoxy group, ethoxy group, propyloxy group, isopropyloxy group, butyloxy group and isobutyloxy group.

Similarly, "alkoxyalkoxy group having 2 to 20 carbon atoms" means an alkoxy group having 1 to 10 carbon atoms that is substituted with an alkoxy group having 1 to 10 carbon atoms. Here, "alkoxy group having 1 to 10 carbon atoms" is the same as defined above. Alkoxyalkoxy groups having 2 to 8 carbon atoms are preferable. Alkoxyalkoxy groups having 2 to 4 carbon atoms are more preferable, with examples including methoxymethoxy group, methoxyethoxy group, ethoxymethoxy group and ethoxyethoxy group.

Similarly, "acyl group having 2 to 11 carbon atoms" means a group —C(=O)—R (wherein R is any of the alkyl groups having 1 to 10 carbon atoms described hereinabove). Examples of the acyl groups having 2 to 11 carbon atoms include acetyl group, propionyl group, butyryl group, valeryl group, hexanoyl group, octanoyl group and decanoyl group (including various isomers). Alkoxycarbonyl groups having 2 to 7 carbon atoms are preferable. Alkoxycarbonyl groups having 2 to 5 carbon atoms are more preferable, with examples including acetyl group, propionyl group, butyryl group, isobutyryl group, valeryl group, isovaleryl group and pivaloyl group.

Similarly, "alkoxycarbonyl group having 2 to 11 carbon atoms" means a group —C(=O)—OR (wherein R is any of the alkyl groups having 1 to 10 carbon atoms described hereinabove). Examples of the alkoxycarbonyl groups having 2 to 11 carbon atoms include methoxycarbonyl group, ethoxycarbonyl group, propoxycarbonyl group, butoxycarbonyl group, pentyloxycarbonyl group, hexyloxycarbonyl group, heptyloxycarbonyl group, octyloxycarbonyl group, nonyloxycarbonyl group and decyloxycarbonyl group (including various isomers). Alkoxycarbonyl groups having 2 to 7 carbon atoms are preferable, with examples including methoxycarbonyl group, ethoxycarbonyl group, propoxycarbonyl group, isopropoxycarbonyl group, butoxycarbonyl group, t-butoxycarbonyl group and hexyloxy group. Alkoxycarbonyl groups having 2 to 5 carbon atoms are more preferable, with examples including methoxycarbonyl group, ethoxycarbonyl group, propoxycarbonyl group, isopropoxycarbonyl group, butoxycarbonyl group and t-butoxycarbonyl group.

Similarly, "alkoxycarbonylalkyl group having 3 to 21 carbon atoms" means an alkyl group having 1 to 10 carbon atoms that is substituted with an alkoxycarbonyl group having 2 to 11 carbon atoms. Here, "alkoxycarbonyl group having 2 to 11 carbon atoms" and "alkyl group having 1 to 10 carbon atoms" are the same as defined above. Alkoxycarbonylalkyl groups having 3 to 11 carbon atoms are preferable. Alkyl groups having 1 to 4 carbon atoms that are substituted with an alkoxycarbonyl group having 2 to 5 carbon atoms (namely, alkoxycarbonylalkyl groups having 3 to 9 carbon atoms) are more preferable, with examples including methoxycarbonylmethyl group, ethoxycarbonylmethyl group, propoxycarbonylmethyl group, isopropoxycarbonylmethyl group, butoxycarbonylmethyl group, t-butoxycarbonylmethyl group, methoxycarbonylethyl group, ethoxycarbonylethyl group, propoxycarbonylethyl group, isopropoxycarbonylethyl group, butoxycarbonylethyl group and t-butoxycarbonylethyl group.

Similarly, "alkoxycarbonylalkoxy group having 3 to 21 carbon atoms" means an alkoxy group having 1 to 10 carbon atoms that is substituted with an alkoxycarbonyl group having 2 to 11 carbon atoms. Here, "alkoxycarbonyl group having 2 to 11 carbon atoms" and "alkoxy group having 1 to 10 carbon atoms" are the same as defined above. Alkoxycarbonylalkoxy groups having 3 to 11 carbon atoms are preferable. Alkoxy groups having 1 to 4 carbon atoms that are substituted with an alkoxycarbonyl group having 2 to 5 carbon atoms (namely, alkoxycarbonylalkoxy groups having 3 to 9 carbon atoms) are more preferable, with examples including methoxycarbonylmethoxy group, ethoxycarbonylmethoxy group, propoxycarbonylmethoxy group, isopropoxycarbonylmethoxy group, butoxycarbonylmethoxy group, t-butoxycarbonylmethoxy group, methoxycarbonylethoxy group, ethoxycarbonylethoxy group, propoxycarbonylethoxy group, isopropoxycarbonylethoxy group, butoxycarbonylethoxy group and t-butoxycarbonylethoxy group.

Similarly, "aryloxy group having 6 to 14 carbon atoms" means a group —OR' (wherein R' is any of the aryls having 6 to 14 carbon atoms described hereinabove). Examples of the aryloxy groups having 6 to 14 carbon atoms include phenoxy group, naphthyloxy group and anthryloxy group. Aryloxy groups having 6 to 10 carbon atoms are preferable, with examples including phenoxy group, 1-naphthyloxy group and 2-naphthyloxy group.

Similarly, "aralkyloxy group having 7 to 14 carbon atoms" means a group —OR" (wherein R" is any of the aralkyl groups described hereinabove). Typical examples include aralkyloxy groups having 7 to 14 carbon atoms, for example, benzyloxy group, phenethyloxy group, phenylpropyloxy group, phenylbutyloxy group, naphthylmethyloxy group and naphthylethyloxy group (including various isomers). Aralkyloxy groups having 7 to 10 carbon atoms are preferable, with examples including benzyloxy group, 1-phenethyloxy group, 2-phenethyloxy group, 3-phenylpropyloxy group and 3-phenylbutyloxy group.

Similarly, "haloalkyl group having 1 to 4 carbon atoms" means an alkyl group having 1 to 4 carbon atoms that is substituted with one or more halogen atoms. Here, "halo" and "alkyl group having 1 to 4 carbon atoms" are the same as defined above. Examples of the haloalkyl groups having 1 to 4 carbon atoms include fluoromethyl group, difluoromethyl group, trifluoromethyl group, 2-fluoroethyl group, 2,2-difluoroethyl group, 2,2,2-trifluoroethyl group, 1,1,2,2,2-pentafluoroethyl group and perfluorobutyl group. Fluoroalkyl groups having 1 to 2 carbon atoms are preferable, with examples including fluoromethyl group, difluoromethyl group, trifluoromethyl group, 2-fluoroethyl group, 2,2-difluoroethyl group, 2,2,2-trifluoroethyl group and 1,1,2,2,2-pentafluoroethyl group.

"Optionally substituted amino group" in the examples of the substituents described above means an amino group or an amino group having one or two substituents. Examples of the substituents include alkyl groups having 1 to 10 carbon atoms; alkoxycarbonylalkyl groups having 3 to 20 carbon atoms; and acyl groups having 2 to 10 carbon atoms. Two substituents may be the same as or different from each other.

In a preferred embodiment of the present invention, $R^1$ in the sulfonamide compounds of the general formulae (1) and (3) is an optionally substituted aryl or heteroaryl group. In a particularly preferred embodiment of the present invention, $R^1$ in the sulfonamide compounds of the general formulae (1) and (3) is an optionally substituted phenyl or pyridyl group.

Examples of the "optionally substituted aryl groups (in particular, phenyl group)" in $R^1$ include aryl groups (in particular, phenyl group); and aryl groups (in particular, phenyl group) substituted with one, two or three substituents selected from the group consisting of halogen atoms, alkyl groups having 1 to 10 carbon atoms, alkenyl groups having 2 to 10 carbon atoms, alkynyl groups having 2 to 10 carbon atoms, optionally substituted aryl groups, optionally substituted heteroaryl groups, optionally substituted aralkyl groups, optionally substituted heteroarylalkyl groups, alkoxy groups having 1 to 10 carbon atoms, alkoxyalkoxy groups having 2 to 20 carbon atoms, acyl groups having 2 to 11 carbon atoms, alkoxycarbonyl groups having 2 to 11 carbon atoms, alkoxycarbonylalkyl groups having 3 to 21 carbon atoms, alkoxycarbonylalkoxy groups having 3 to 21 carbon atoms, aryloxy groups having 6 to 14 carbon atoms, aralkyloxy groups having 7 to 14 carbon atoms, haloalkyl groups having 1 to 4 carbon atoms, optionally substituted amino groups, cyano groups and nitro groups. Here, two or more of the substituents may be the same as or different from one another. Any two substituents bonded to adjacent ring atoms may form a ring together with such ring atoms.

"Optionally substituted aryl group (in particular, phenyl group)" in $R^1$ is preferably an aryl group having 6 to 10 carbon atoms (in particular, a phenyl group); or an aryl group having 6 to 10 carbon atoms (in particular, a phenyl group) substituted with one, two or three substituents selected from the group consisting of halogen atoms, alkyl groups having 1 to 4 carbon atoms, alkoxy groups having 1 to 4 carbon atoms, and nitro groups. Two or more of the substituents may be the same as or different from one another.

The optionally substituted aryl group in $R^1$ is more preferably a phenyl group, a 1-naphthyl group, a 2-naphthyl group, a 4-tolyl group, a 3-fluorophenyl group, a 4-fluorophenyl group, a 4-chlorophenyl group, a 4-methoxyphenyl group, a 3,4-dimethoxyphenyl group, a 3,4-methylenedioxyphenyl group or a 4-nitrophenyl group, and is more preferably a phenyl group, a 3-fluorophenyl group or a 4-fluorophenyl group.

Examples of the "optionally substituted heteroaryl groups (in particular, pyridyl group)" in by $R^1$ include heteroaryl groups (in particular, pyridyl group); and heteroaryl groups (in particular, pyridyl group) substituted with one, two or three substituents selected from the group consisting of halogen atoms, alkyl groups having 1 to 10 carbon atoms, alkenyl groups having 2 to 10 carbon atoms, alkynyl groups having 2 to 10 carbon atoms, optionally substituted aryl groups, optionally substituted heteroaryl groups, optionally substituted aralkyl groups, optionally substituted heteroarylalkyl groups, alkoxy groups having 1 to 10 carbon atoms, alkoxyalkoxy groups having 2 to 20 carbon atoms, acyl groups having 2 to 11 carbon atoms, alkoxycarbonyl groups having 2 to 11 carbon atoms, alkoxycarbonylalkyl groups having 3 to 21 carbon atoms, alkoxycarbonylalkoxy groups having 3 to 21 carbon atoms, aryloxy groups having 6 to 14 carbon atoms, aralkyloxy groups having 7 to 14 carbon atoms, haloalkyl groups having 1 to 4 carbon atoms, optionally substituted amino groups, cyano groups and nitro groups. Here, two or more of the substituents may be the same as or different from one another. Any two substituents bonded to adjacent ring atoms may form a ring together with such ring atoms.

The "optionally substituted heteroaryl group (in particular, pyridyl group)" in $R^1$ is preferably a 5- to 10-membered heteroaryl group (in particular, a pyridyl group); or a 5- to 10-membered heteroaryl group (in particular, a pyridyl group) substituted with one, two or three substituents selected from the group consisting of halogen atoms, alkyl groups having 1 to 4 carbon atoms, alkoxy groups having 1 to 4 carbon atoms, cyano groups and nitro groups. Two or more of the substituents may be the same as or different from one another.

The optionally substituted heteroaryl group in $R^1$ is more preferably a 2-pyridyl group, a 3-pyridyl group, a 4-pyridyl group, a 2-pyrrolyl group, a 3-pyrrolyl group, a 2-thienyl group, a 3-thienyl group, a 2-furyl group, a 2-(3-methyl)pyridyl group, a 2-(4-methyl)pyridyl group, a 3-(2-methyl)pyridyl group, a 2-(3-fluoro)pyridyl group or a 2-(3-nitro)pyridyl group, and is more preferably a 2-pyridyl group or a 3-pyridyl group.

In a preferred embodiment of the present invention, $R^2$ in the sulfonamide compounds of the general formulae (1) and (3) is an optionally substituted aralkyl or heteroarylalkyl group. In a particularly preferred embodiment of the present invention, $R^2$ in the sulfonamide compounds of the general formulae (1) and (3) is an optionally substituted benzyl or benzofuranylmethyl group.

Examples of the "optionally substituted aralkyl groups (in particular, benzyl group)" in $R^2$ include aralkyl groups (in particular, benzyl group); and aralkyl groups (in particular, benzyl group) substituted with one, two or three substituents selected from the group consisting of halogen atoms, alkyl groups having 1 to 10 carbon atoms, alkenyl groups having 2 to 10 carbon atoms, alkynyl groups having 2 to 10 carbon atoms, optionally substituted aryl groups, optionally substituted heteroaryl groups, optionally substituted aralkyl groups, optionally substituted heteroarylalkyl groups, alkoxy groups having 1 to 10 carbon atoms, alkoxyalkoxy groups having 2 to 20 carbon atoms, aryloxy groups having 6 to 14 carbon atoms, aralkyloxy groups having 7 to 14 carbon atoms, haloalkyl groups having 1 to 4 carbon atoms, cyano groups and nitro groups. Here, two or more of the substituents may be the same as or different from one another. Any two substituents bonded to adjacent ring atoms may form a ring together with such ring atoms.

The "optionally substituted aralkyl group (in particular, benzyl group)" in $R^2$ is preferably an aralkyl group having 7 to 10 carbon atoms (in particular, a benzyl group); or an aralkyl group having 7 to 10 carbon atoms (in particular, a benzyl group) substituted with one, two or three substituents selected from the group consisting of halogen atoms, alkyl groups having 1 to 4 carbon atoms, optionally substituted aryl groups, optionally substituted heteroaryl groups, alkoxy groups having 1 to 4 carbon atoms, alkoxyalkoxy groups having 2 to 4 carbon atoms, aryloxy groups having 6 to 10 carbon atoms, aralkyloxy groups having 7 to 10 carbon atoms, haloalkyl groups having 1 to 4 carbon atoms, cyano groups and nitro groups. Two or more of the substituents may be the same as or different from one another.

The "optionally substituted aralkyl group (in particular, benzyl group)" in $R^2$ is more preferably an aralkyl group having 7 to 10 carbon atoms (in particular, a benzyl group); or an aralkyl group having 7 to 10 carbon atoms (in particular, a benzyl group) substituted with an optionally substituted aryl group or an optionally substituted heteroaryl group.

The optionally substituted aralkyl group in $R^2$ is still more preferably a benzyl group, a phenethyl group, a 3-phenylpropyl group or a 4-phenylbutyl group; a biphenyl-4-ylmethyl group, a 2'-ethoxybiphenyl-4-ylmethyl group, a 3'-ethoxybiphenyl-4-ylmethyl group, a 4'-ethoxybiphenyl-4-ylmethyl group, a 2'-(1-propenyl)biphenyl-4-ylmethyl group, a 2'-(1-propenyl)biphenyl-4-ylmethyl group, a 3'-(1-propenyl)biphenyl-4-ylmethyl group, a 4'-(1-propenyl)biphenyl-4-ylmethyl group, a 2'-(1-propynyl)biphenyl-4-ylmethyl group, a 3'-(1-propynyl)biphenyl-4-ylmethyl group or a 4'-(1-propynyl)biphenyl-4-ylmethyl group; a 4-(thiazol-2-yl)benzyl group, a 3-(thiazol-2-yl)benzyl group, a 2-(thiazol-2-yl)benzyl group, a 4-(thiazol-4-yl)benzyl group, a 4-(4-methylthiazol-2-yl)benzyl group, a 4-(5-methylthiazol-2-yl)benzyl group, a 4-(4,5-dimethylthiazol-2-yl)benzyl group, a 4-(5-fluorothiazol-2-yl)benzyl group, a 4-(5-chlorothiazol-2-yl)benzyl group, a 4-(4-trifluoromethylthiazol-2-yl)benzyl group, a 4-(5-trifluoromethylmethylthiazol-2-yl)benzyl group, a 4-((1H)-pyrazol-1-yl)benzyl group, a 3-((1H)-pyrazol-1-yl)benzyl group, a 2-((1H)-pyrazol-1-yl) benzyl group, a 4-(3-methyl-(1H)-pyrazol-1-yl)benzyl group, a 4-(5-methyl-(1H)-pyrazol-1-yl)benzyl group, a 4-(oxazol-1-yl)benzyl group, a 3-(oxazol-1-yl)benzyl group, a 2-(oxazol-1-yl)benzyl group, a 4-(5-methyloxazol-1-yl) benzyl group or a 4-(4-methyloxazol-1-yl)benzyl group.

Examples of the "optionally substituted heteroarylalkyl groups (in particular, benzofuranylmethyl group)" in $R^2$ include heteroarylalkyl groups (in particular, benzofuranylmethyl group); and heteroarylalkyl groups (in particular, benzofuranyl group) substituted with one, two or three substituents selected from the group consisting of halogen atoms, alkyl groups having 1 to 10 carbon atoms, alkenyl groups having 2 to 10 carbon atoms, alkynyl groups having 2 to 10 carbon atoms, optionally substituted aryl groups, optionally substituted heteroaryl groups, optionally substituted aralkyl groups, optionally substituted heteroarylalkyl groups, alkoxy groups having 1 to 10 carbon atoms, alkoxyalkoxy groups having 2 to 20 carbon atoms, acyl groups having 2 to 11 carbon atoms, alkoxycarbonyl groups having 2 to 11 carbon atoms, alkoxycarbonylalkyl groups having 3 to 21 carbon atoms, alkoxycarbonylalkoxy groups having 3 to 21 carbon atoms, aryloxy groups having 6 to 14 carbon atoms, aralkyloxy groups having 7 to 14 carbon atoms, haloalkyl groups having 1 to 4 carbon atoms, optionally substituted amino groups, cyano groups and nitro groups. Here, two or more of the substituents may be the same as or different from one another. Any two substituents bonded to adjacent ring atoms may form a ring together with such ring atoms.

The "optionally substituted heteroarylalkyl group (in particular, benzofuranylmethyl group)" in $R^2$ is preferably a 6- to 10-membered heteroarylalkyl group (in particular, a benzofuranylmethyl group); or a 6- to 10-membered heteroarylalkyl group (in particular, a benzofuranylmethyl group) substituted with one, two or three substituents selected from the group consisting of halogen atoms, alkyl groups having 1 to 4 carbon atoms, optionally substituted aryl groups, optionally substituted heteroaryl groups, alkoxy groups having 1 to 4 carbon atoms, alkoxyalkoxy groups having 2 to 4 carbon atoms, aryloxy groups having 6 to 10 carbon atoms, aralkyloxy groups having 7 to 10 carbon atoms, haloalkyl groups having 1 to 4 carbon atoms, cyano groups and nitro groups. Two or more of the substituents may be the same as or different from one another.

The optionally substituted heteroarylalkyl group in $R^2$ is more preferably a 2-pyridylmethyl group, a 3-pyridylmethyl group, a 2-pyrimidinylmethyl group, a 5-pyrimidinylmethyl group, a 3-pyridazinylmethyl group, a 2-indolylmethyl group, a 5-indolylmethyl group, a 2-benzofuranylmethyl group, a 5-indolylmethyl group, a 2-benzothienylmethyl group, a 5-benzothienylmethyl group, a 6-fluoro-2-benzofuranylmethyl group, a 6-chloro-2-benzofuranylmethyl group, a 6-methoxy-2-benzofuranylmethyl group, a 6-fluoro-2-benzothienylmethyl group, a 6-chloro-2-benzothienylmethyl group, a 6-methoxy-2-benzothienylmethyl group or a 6-phenyl-3-pyridazinylmethyl group.

In the compound of the general formula (2), X is a halogen atom, preferably a chlorine atom, a bromine atom or an iodine atom, and is more preferably a chlorine atom.

In the compounds of the general formulae (2) and (3), $R^3$ is an optionally substituted alkyl, aralkyl or heteroarylalkyl group.

Examples of the substituents in the "optionally substituted alkyl groups" in $R^3$ include halogen atoms; alkoxy groups having 1 to 10 carbon atoms; cyano groups; and nitro groups. Two or more of the substituents may be the same as or different from one another.

In a preferred embodiment of the present invention, $R^3$ in the compounds of the general formulae (2) and (3) is an optionally substituted aralkyl or heteroarylalkyl group. In a particularly preferred embodiment of the present invention, $R^3$ in the compounds of the general formulae (2) and (3) is an optionally substituted benzyl or pyridylmethyl group.

Examples of the substituents in the "optionally substituted aralkyl groups (in particular, benzyl group)" and the "optionally substituted heteroarylalkyl groups (in particular, pyridylmethyl group)" in $R^3$ include halogen atoms; alkyl groups having 1 to 10 carbon atoms; alkenyl groups having 2 to 10 carbon atoms; alkynyl groups having 2 to 10 carbon atoms; optionally substituted aryl groups; optionally substituted heteroaryl groups; optionally substituted aralkyl groups; optionally substituted heteroarylalkyl groups; alkoxy groups having 1 to 10 carbon atoms; alkoxyalkoxy groups having 2 to 20 carbon atoms; acyl groups having 2 to 11 carbon atoms; alkoxycarbonyl groups having 2 to 11 carbon atoms; alkoxycarbonylalkyl groups having 3 to 21 carbon atoms; alkoxycarbonylalkoxy groups having 3 to 21 carbon atoms; aryloxy groups having 6 to 14 carbon atoms; aralkyloxy groups having 7 to 14 carbon atoms; haloalkyl groups having 1 to 4 carbon atoms; optionally substituted amino groups; cyano groups; and nitro groups. Here, two or more of the substituents may be the same as or different from one another. Any two substituents bonded to adjacent ring atoms may form a ring together with such ring atoms.

The "optionally substituted aralkyl group" in $R^3$ is preferably an aralkyl group having 7 to 14 carbon atoms (in particular, a benzyl group); or an aralkyl group having 7 to 14 carbon atoms (in particular, a benzyl group) substituted with one, two or three substituents selected from the group consisting of halogen atoms, alkyl groups having 1 to 10 carbon atoms, alkoxy groups having 1 to 10 carbon atoms, alkoxycarbonylalkyl groups having 3 to 21 carbon atoms, alkoxycarbonylalkoxy groups having 3 to 21 carbon atoms, haloalkyl groups having 1 to 4 carbon atoms, optionally substituted amino groups, cyano groups and nitro groups. Two or more of the substituents may be the same as or different from one another. Any two substituents bonded to adjacent ring atoms may form a ring together with such ring atoms.

The "optionally substituted heteroarylalkyl group" in $R^3$ is preferably a 6- to 14-membered heteroarylalkyl group (in particular, a pyridylmethyl group); or an aralkyl group having 7 to 14 carbon atoms (in particular, a benzyl group) substituted with one, two or three substituents selected from the group consisting of halogen atoms, alkyl groups having 1 to 10 carbon atoms, alkoxy groups having 1 to 10 carbon atoms, alkoxycarbonylalkoxy groups having 3 to 21 carbon atoms, haloalkyl groups having 1 to 4 carbon atoms, optionally substituted amino groups, cyano groups and nitro groups. Two or more of the substituents may be the same as or different from one another. Any two substituents bonded to adjacent ring atoms may form a ring together with such ring atoms.

Examples of the "optionally substituted heteroarylalkyl groups" in $R^3$ include 2-pyridylmethyl, 3-pyridylmethyl, 4-pyridylmethyl, 2-(3-methyl)furylmethyl group, 2-(4-methyl)furylmethyl group, 2-(3-ethyl)furylmethyl group, 2-(4-ethyl)furylmethyl group, 2-(3-fluoro)furylmethyl group, 2-(3-chloro)furylmethyl group, 2-(3-methoxy)furylmethyl group, 2-(3-nitro)furylmethyl group, 2-(3-cyano)furylmethyl group, 2-(3-methyl)pyridylmethyl group, 2-(4-methyl)pyridylmethyl group, 2-(3-ethyl)pyridylmethyl group, 2-(4-ethyl)pyridylmethyl group, 2-(3-fluoro)pyridylmethyl group, 2-(4-chloro)pyridylmethyl group, 2-(3-methoxy)pyridylmethyl group, 2-(3-nitro)pyridylmethyl group, 2-(3-cyano)pyridylmethyl group, 2-(3,5-dichloro)pyridylmethyl group, 3-(2-chloro)pyridylmethyl group, 2-(3-methyl)pyrrolylmethyl group, 2-(3-methyl)thienylmethyl group, 2-(6-methoxycarbonylmethylamino)pyridylmethyl group, 2-(6-ethoxycarbonylmethylamino)pyridylmethyl group, 2-(6-propoxycarbonylmethylamino)pyridylmethyl group, 2-(6-isopropoxycarbonylmethylamino)pyridylmethyl group, 2-(6-t-butoxycarbonylmethylamino)pyridylmethyl group and 2-(6-hexyloxycarbonylmethylamino)pyridylmethyl group, with 2-(3-methyl)furylmethyl group, 2-(3-fluoro)furylmethyl group, 2-(3-methyl)pyridylmethyl group, 2-(3-fluoro)pyridylmethyl group, 2-(3-nitro)pyridyl group, 2-(3-cyano)pyridylmethyl group, 2-(3,5-dichloro)pyridylmethyl group, 2-(6-methoxycarbonylmethylamino)pyridylmethyl group, 2-(6-ethoxycarbonylmethylamino)pyridylmethyl group, 2-(6-propoxycarbonylmethylamino)pyridylmethyl group, 2-(6-isopropoxycarbonylmethylamino)pyridylmethyl group, 2-(6-t-butoxycarbonylmethylamino)pyridylmethyl group and 2-(6-hexyloxycarbonylmethylamino)pyridylmethyl group being preferable.

The optionally substituted heteroarylalkyl group in $R^3$ is more preferably 2-pyridylmethyl, 3-pyridylmethyl, 4-pyridylmethyl, a 2-(6-methoxycarbonylmethylamino)pyridylmethyl group, a 2-(6-ethoxycarbonylmethylamino)pyridylmethyl group, a 2-(6-propoxycarbonylmethylamino)pyridylmethyl group, a 2-(6-isopropoxycarbonylmethylamino)pyridylmethyl group, a 2-(6-t-butoxycarbonylmethylamino)pyridylmethyl group or a 2-(6-hexyloxycarbonylmethylamino)pyridylmethyl group.

In a preferred embodiment of the present invention, the sulfonamide compound of the general formula (1) is of the general formula (4):

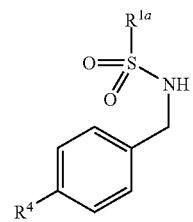

(4)

(In the formula,
$R^{1a}$ is defined the same as $R^1$, and
$R^4$ is an optionally substituted aryl or heteroaryl group.)

In a preferred embodiment of the present invention, the halogenated organic compound of the general formula (2) is of the general formula (5):

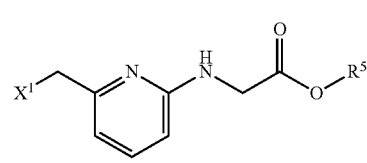

(5)

(In the formula, $R^5$ is an alkyl group, and $X^1$ is defined the same as X.)

In a preferred embodiment of the present invention, the N-substituted sulfonamide compound of the general formula (3) is of the general formula (6):

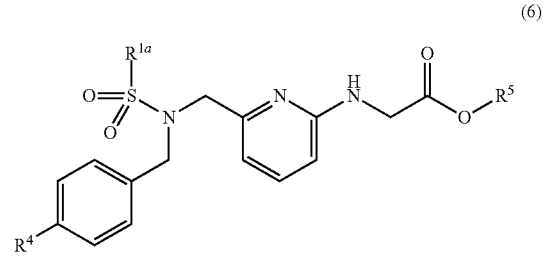

(6)

(In the formula, $R^{1a}$, $R^4$ and $R^5$ are the same as defined above.)

In the general formulae (4) and (6), $R^{1a}$ is defined the same as $R^1$.

In the general formulae (4) and (6), $R^4$ is an optionally substituted aryl or heteroaryl group.

Examples of the substituents in the "optionally substituted aryl groups" and the "optionally substituted heteroaryl groups" in $R^4$ include halogen atoms; alkyl groups having 1 to 10 carbon atoms; alkenyl groups having 2 to 10 carbon atoms; alkynyl groups having 2 to 10 carbon atoms; alkoxy groups having 1 to 10 carbon atoms; haloalkyl groups having 1 to 4 carbon atoms; cyano groups; and nitro groups. Two or more of the substituents may be the same as or different from one another.

Examples of the "optionally substituted heteroaryl groups" in $R^4$ include thiazole group, oxazole group, benzothiazole group, benzopyridoxinethiazole group, pyridoxinethiazole group, pyridine group, pyridazine group, pyrimidine group, pyrazine group, triazine group, quinoline group, pyridobenzothiazole group and pyrazole group (including various isomers), and further include 2-(4-methyl)thiazole group, 2-(5-methyl)thiazole group, 2-(5-fluoro)thiazole group, (1H)-1-(3-methyl)pyrazole group, 1H-1-(5-methyl) pyrazole group, 2-(4-methyl)oxazole group and 2-(5-methyl)oxazole group.

The "optionally substituted heteroaryl group" in $R^4$ is preferably a 2-thiazole group, a 2-(4-methyl)thiazole group, a 2-(5-fluoro)thiazole group, a 1H-1-pyrazole group, a 1H-(3-methyl)pyrazole group or a 2-methoxythiazole group.

In the general formulae (5) and (6), $R^5$ is an alkyl group, for example, an alkyl group having 1 to 10 carbon atoms, and is preferably an alkyl group having 1 to 6 carbon atoms, for example, a methyl group, an ethyl group, an n-propyl group, an isopropyl group, a t-butyl group or an n-hexyl group.

In the general formula (5), $X^1$ is defined the same as X.

The reaction in the present invention is carried out in the presence of cesium carbonate or potassium carbonate. Cesium carbonate is more preferable.

In the present invention, cesium carbonate or potassium carbonate is preferably used in an amount of 0.5 to 10 mol, more preferably 0.5 to 5 mol, and particularly preferably 1 to 3 mol per 1 mol of the sulfonamide compound of the general formula (1) or (4).

The cesium carbonate or the potassium carbonate used in the present invention may be an anhydride or a hydrate, and is preferably an anhydride.

The purity of the cesium carbonate or the potassium carbonate used in the present invention is not particularly limited, but is preferably not less than 95%, and more preferably not less than 98%.

The reaction in the present invention is performed in the presence of an organic solvent. The organic solvent used in the reaction of the present invention is not particularly limited as long as it is inert in the reaction.

Examples of the organic solvents used in the present invention include alcohol organic solvents such as methanol, ethanol, propanol, 2-propanol, butyl alcohol and t-butyl alcohol; nitrile organic solvents such as acetonitrile and benzonitrile; amide solvents such as N,N-dimethylformamide, N,N-dimethylacetamide, N-methylpyridone, dimethylimidazole and 1,3-dimethyl-2-imidazolidinone; halogenated organic solvents such as methylene chloride, chloroform and 1,2-dichloroethane; aliphatic hydrocarbon solvents such as pentane, hexane, heptane, octane, cyclopentane, cyclohexane and cyclopentane; aromatic hydrocarbon solvents such as benzene, toluene and xylene; and ether solvents such as diethyl ether, t-butyl methyl ether, diisopropyl ether, tetrahydrofuran and 1,4-dioxane. Alcohol organic solvents, aromatic hydrocarbon organic solvents, halogenated organic solvents and nitrile organic solvents are preferable, and nitrile organic solvents are more preferable. Incidentally, these organic solvents may be used singly, or two or more may be used in combination.

The organic solvent is preferably used in an amount of 2 to 200 mL, more preferably 5 to 50 mL, and particularly preferably 5 to 20 mL per 1 g of the sulfonamide compound of the general formula (1) or (4).

The reaction in the present invention is performed by, for example, mixing a sulfonamide compound of the general formula (1) or (4), a halogenated organic compound of the general formula (2) or (5), cesium carbonate or potassium carbonate, and an organic solvent, and allowing the compounds to react together while performing stirring. Here, the reaction pressure is not particularly limited, but normal pressure is preferable.

In the reaction of the present invention, the reaction temperature is, for example, −20 to 130° C., preferably 0 to 90° C., more preferably 30 to 90° C., and particularly preferably 60 to 90° C.

The reaction system in the present invention is generally a solid-liquid heterogeneous system. After the completion of the reaction, the product may be recovered with high purity easily by filtering the system to remove cesium carbonate or potassium carbonate, and subjecting the filtrate to concentration, extraction or crystallization.

The production apparatus used in the reaction of the present invention is not particularly limited. For example, use may be made of a usual production apparatus including a reaction vessel, a heating (cooling) device and a distillation device (for example, a Dean-Stark trap).

An N-substituted sulfonamide compound of the general formula (3) or (6) that is obtained by the method of the present invention may be further purified by a usual method such as distillation, separation, extraction, crystallization, recrystallization or column chromatography.

In the production method of the present invention, the N-substituted sulfonamide compound of the general formula (3) or (6) is obtained selectively by the use of cesium carbonate or potassium carbonate. Thus, the compound contains an extremely small amount of byproduced contaminants which arise from side reactions as often experienced in the conventional production methods and are difficult to remove, and thereby attains higher safety as a medicinal product.

Preferably, the N-substituted sulfonamide compound of the general formula (3) or (6) that is obtained by the production method of the present invention has an HPLC purity of not less than 99.5%, and the contents of any impurities present in the compound are each less than 0.10%. More preferably, the HPLC purity is not less than 99.9%.

Thus, the present invention may provide a high-purity N-substituted sulfonamide compound of the general formula (3) or (6). The N-substituted sulfonamide compound of the general formula (3) or (6) according to the present invention has high purity; preferably, the HPLC purity thereof is not less than 99.5% and the contents of any impurities present in the compound are each less than 0.10%. More preferably, the HPLC purity is not less than 99.9%.

The present invention may provide a halogenated organic compound of the general formula (5), and a hydroxymethyl compound that is a raw material for the halogenated organic compound. Such compounds are of the general formula (9):

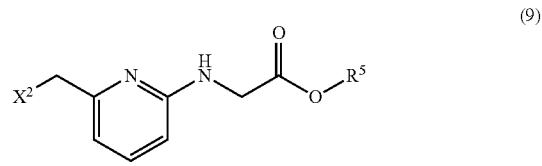

(9)

(In the formula, $R^5$ is an alkyl group, and $X^2$ is a halogen atom or a hydroxyl group.) In the general formula (9), $R^5$ is an alkyl group, for example, an alkyl group having 1 to 10 carbon atoms, and is preferably an alkyl group having 1 to 6 carbon atoms, for example, a methyl group, an ethyl group, an n-propyl group, an isopropyl group, a t-butyl group or an n-hexyl group. $X^2$ is a halogen atom, and is preferably a chlorine atom or a bromine atom. Specific embodiments of the compounds of the general formula (9) are disclosed in Examples below.

EXAMPLES

Next, the present invention will be described in detail by presenting Examples, but the scope of the present invention is not limited thereto.

The structure of target compounds obtained was identified by methods such as IR and NMR spectral analysis. Further, the reaction yields (internal standard method) and the chemical purities were measured using high-performance liquid chromatography (HPLC).

Example 1

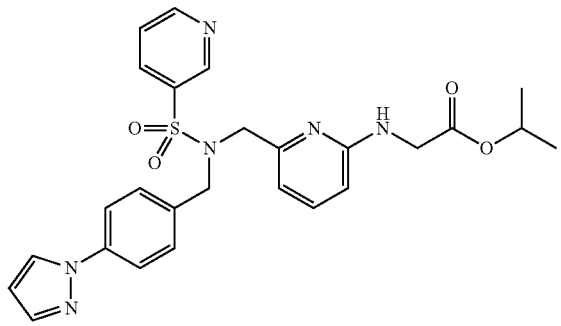 [SMILES: CC(C)OC(=O)CNc1cccc(CN(Cc2ccc(-n3cccn3)cc2)S(=O)(=O)c2cccnc2)n1]

Synthesis of Isopropyl 2-{[6-({N-[4-(1H-pyrazol-1-yl)benzyl]pyridine-3-sulfonamido}methyl)pyridin-2-yl]amino}acetate A glass vessel having an internal volume of about 50 ml and equipped with a stirrer, a thermometer and an upper cooling unit was loaded with 3.21 g (10.2 mmol) of N-[4-(1H-pyrazol-1-yl)benzyl]pyridine-3-sulfonamide, 2.43 g (10.0 mmol) of isopropyl 2-{[6-(chloromethyl)pyridin-2-yl]amino}acetate obtained in Example 6, 6.65 g (20.4 mmol) of cesium carbonate and 17.6 g of acetonitrile. The mixture was stirred while performing heating at 80° C. The reaction was performed for 2 hours until the area percentage of the raw material isopropyl 2-{[6-(chloromethyl)pyridin-2-yl]amino}acetate in the high-performance liquid chromatography analysis fell to 0.03% or less. The reaction was further carried out for 2 hours. The reaction conversions of isopropyl 2-{[6-(chloromethyl)pyridin-2-yl]amino}acetate after 1 hour and 2 hours from the start of the thermal stirring were 99.88% and 99.97%, respectively. After the completion of the reaction, the reaction liquid was cooled to room temperature and was filtered through Celite (trade name), and the residue was washed with acetonitrile. The filtrate obtained was quantitatively analyzed by high-performance liquid chromatography, and was found to contain 5.08 g of the target product (97.5% reaction yield). Next, the reaction liquid was concentrated under reduced pressure until the weight of the liquid became 7.85 g. After the addition of 42.8 g of toluene, the product was washed with water three times. The resultant organic phase was combined with 31.5 ml (31.5 mmol) of 1 mol/L hydrochloric acid. The mixture was stirred at room temperature for 20 minutes and was separated. The separated organic phase contained 0.17 g of the target product (corresponding to 3.2% yield). To the aqueous phase were added 42.8 g of toluene and 34.6 ml (34.6 mmol) of a 1 mol/L aqueous sodium hydroxide solution. The mixture was heated to 40° C. and was stirred for 20 minutes. Hot filtration was performed at 40° C., and thereafter the liquid was separated. The organic phase obtained was washed with water two times. The organic phase was concentrated under reduced pressure until the weight of the liquid became 8.97 g, and 7.40 g of 2-propanol was added. The mixture was heated to 60° C., then cooled gradually, stirred at 33° C. for 30 minutes, cooled slowly to not more than 5° C., and stirred at the temperature for 1 hour. The solid precipitated was recovered by filtration, washed with cold 2-propanol, and vacuum dried at 50° C. to give 3.90 g of isopropyl 2-{[6-({N-[4-(1H-pyrazol-1-yl)benzyl]pyridine-3-sulfonamido}methyl)pyridin-2-yl]amino}acetate as a light brown solid (75.1% yield of isolation in terms of the raw material isopropyl 2-{[6-(chloromethyl)pyridin-2-yl]amino}acetate). The high-performance chromatography HPLC showed that the quantitative purity was 99.5% and the compound contained 0.04% of the raw material N-[4-(1H-pyrazol-1-yl)benzyl]pyridine-3-sulfonamide. In the measurement by high-performance liquid chromatography HPLC (260 nm wavelength), no impurities having an area percentage of 0.1% or above were detected.

The properties of isopropyl 2-{[6-({N-[4-(1H-pyrazol-1-yl)benzyl]pyridine-3-sulfonamido}methyl)pyridin-2-yl]amino}acetate obtained are described below.

EI-MS (m/z): 520 [M].

CI-MS (m/z): 521 [M+1].

$^1$H-NMR (CDCl$_3$, δ (ppm)): 1.24 (6H, d, J=6.3 Hz), 3.82 (2H, d, J=5.5 Hz), 4.31 (2H, s), 4.64 (2H, s), 4.94 (1H, t, J=5.5 Hz), 5.07 (1H, sep, J=6.3 Hz), 6.26 (1H, d, J=8.3 Hz), 6.41 (1H, dd, J=7.2, 0.5 Hz), 6.46 (1H, dd, J=2.5, 1.8 Hz), 7.25 (1H, dd, J=8.3, 7.2 Hz), 7.32 (1H, ddd, J=8.0, 4.9, 0.8 Hz), 7.37-7.42 (2H, m), 7.62-7.66 (2H, m), 7.71 (1H, dd, J=1.8, 0.6 Hz), 7.93 (1H, dd, J=2.6, 0.6 Hz), 7.94 (1H, ddd, J=8.0, 2.4, 1.7 Hz), 8.69 (1H, dd, J=4.8, 1.6 Hz), 8.98 (1H, dd, J=2.4, 0.8 Hz).

$^{13}$C-NMR (CDCl$_3$, δ (ppm)): 21.8, 43.7, 51.0, 51.1, 68.9, 107.4, 107.7, 112.6, 119.2, 123.3, 126.7, 129.9, 133.8, 134.6, 137.3, 137.6, 139.8, 141.1, 148.0, 152.6, 153.2, 157.3, 170.5.

IR (KBr cm$^{-1}$): 764 (C—H), 1161 (S=O), 1525 (C=N), 1737 (C=O), (2981, 2933) (C—H), 3437 (N—H).

Elemental analysis: Calcd: C, 59.80%; H, 5.31%; N, 16.07%.

Found: C, 59.98%; H, 5.42%; N, 16.14%.

Example 2

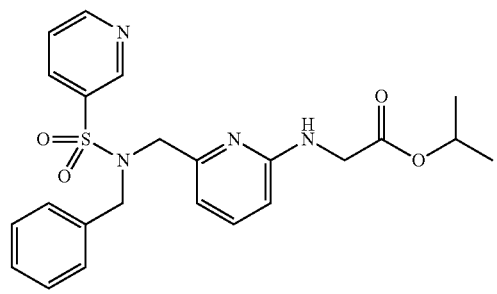 [SMILES: CC(C)OC(=O)CNc1cccc(CN(Cc2ccccc2)S(=O)(=O)c2cccnc2)n1]

Synthesis of Isopropyl 2-({6-[(N-benzylpyridine-3-sulfonamido)methyl]pyridin-2-yl}amino)acetate A glass vessel having an internal volume of about 50 ml and equipped with a stirrer, a thermometer and an upper cooling unit was loaded with 0.253 g (1.02 mmol) of N-benzylpyridine-3-sulfonamide, 0.243 g (1.00 mmol) of isopropyl 2-{[6-(chloromethyl)pyridin-2-yl]amino}acetate obtained in Example 6, 0.665 g (2.04 mmol) of cesium carbonate and 1.76 g of acetonitrile. The mixture was stirred while performing heating at 80° C. The reaction was performed for 2 hours until the area percentage of the raw material isopropyl 2-{[6-(chloromethyl)pyridin-2-yl]amino}acetate in the high-performance liquid chromatography analysis fell to 0.03% or less. The reaction was further carried out for 2 hours. The reaction conversions of isopropyl 2-{[6-(chloromethyl)pyridin-2-yl]amino}acetate after 1 hour and 2 hours from the start of the thermal stirring were 99.81% and at least 99.99%, respectively. After the completion of the reaction, the reaction liquid was cooled to room temperature and was filtered through Celite (trade name), and the residue was washed with acetonitrile. The filtrate obtained was quantitatively analyzed by high-performance liquid chromatography, and was found to contain 0.430 g of the target product (94.5% reaction yield). Next, the reaction liquid was concentrated under reduced pressure until the weight of the liquid became 0.785 g. After the addition of 4.3 g of toluene, the product was washed with water three times. During this process, an emulsion was formed. Although this emulsion contained a portion of the target product, it was disposed of together with the aqueous phase. The resultant organic phase was combined with 3.15 ml (3.15 mmol) of 1 mol/L hydrochloric acid. The mixture was stirred at room temperature for 20 minutes and was separated. To the aqueous phase were added 4.27 g of toluene and 3.46 ml (3.46 mmol) of a 1 mol/L aqueous sodium hydroxide solution. The mixture was heated to 40° C. and was stirred for 20 minutes. The liquid was separated. The organic phase obtained was washed with water two times. The organic phase was concentrated under reduced pressure until the weight of the liquid became 0.239 g. In this manner, isopropyl 2-({6-[(N-benzylpyridine-3-sulfonamido)methyl]pyridin-2-yl}amino)acetate was obtained as a light brown solid (53.8% yield of isolation in terms of the raw material isopropyl 2-{[6-(chloromethyl)pyridin-2-yl]amino}acetate). The high-performance liquid chromatography HPLC showed that the quantitative purity was 98.0%. In the measurement by high-performance liquid chromatography HPLC (260 nm wavelength), no impurities having an area percentage of 0.1% or above were detected.

The properties of isopropyl 2-({6-[(N-benzylpyridine-3-sulfonamido)methyl]pyridin-2-yl}amino)acetate obtained are described below.

EI-MS (m/z): 454 [M].
CI-MS (m/z): 455 [M+1].
$^1$H-NMR (CDCl$_3$, δ (ppm)): 1.27 (6H, d, J=6.3 Hz), 3.82 (2H, d, J=5.4 Hz), 4.31 (2H, s), 4.62 (2H, s), 4.73 (1H, t, J=5.2 Hz), 5.09 (1H, sep, J=6.3 Hz), 6.26 (1H, d, J=8.1 Hz), 6.43 (1H, d, J=6.9 Hz), 7.26-7.33 (7H, m), 7.90-7.93 (1H, m), 8.69 (1H, dd, J=4.8, 1.6 Hz), 8.95 (1H, dd, J=2.3, 0.7 Hz).
$^{13}$C-NMR (CDCl$_3$, δ (ppm)): 21.8, 43.8, 51.1, 51.6, 69.0, 107.2, 112.6, 123.2, 127.9, 128.6, 128.8, 134.7, 135.6, 137.6, 137.7, 148.2, 152.5, 153.6, 157.3, 170.5.
IR (KBr cm$^{-1}$): 1169 (S=O), 1724 (C=O), (2936, 2984) (C—H), 3428 (N—H).

Elemental analysis: Calcd: C, 60.77%; H, 5.77%; N, 12.33%.
Found: C, 61.03%; H, 5.85%; N, 12.15%.

Example 3

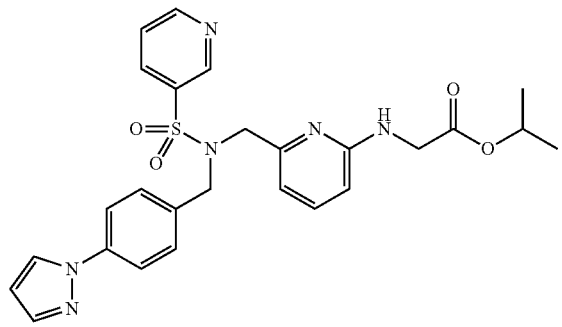 [SMILES: CC(C)OC(=O)CNc1cccc(CN(Cc2ccc(-n3cccn3)cc2)S(=O)(=O)c2cccnc2)n1]

Synthesis of Isopropyl 2-{[6-({N-[4-(1H-pyrazol-1-yl)benzyl]pyridine-3-sulfonamido}methyl)pyridin-2-yl]amino}acetate A glass vessel having an internal volume of about 30 ml and equipped with a stirrer, a thermometer and an upper cooling unit was loaded with 641 mg (2.04 mmol) of N-[4-(1H-pyrazol-1-yl)benzyl]pyridine-3-sulfonamide, 485 mg (2.00 mmol) of isopropyl 2-{[6-(chloromethyl)pyridin-2-yl]amino}acetate obtained in Example 6, 1.33 g (4.08 mmol) of cesium carbonate and 3.53 g of acetonitrile. The mixture was stirred at 30° C. The reaction was performed for 26 hours until the area percentage of the raw material isopropyl 2-{[6-(chloromethyl)pyridin-2-yl]amino}acetate in the high-performance liquid chromatography analysis fell to 0.3% or less. The reaction was further carried out for 2 hours. After the completion of the reaction, the reaction liquid was filtered, and the residue was washed with acetonitrile. The filtrate obtained was quantitatively analyzed by high-performance liquid chromatography, and was found to contain 991 mg of the target product (95.2% reaction yield).

Example 4

Synthesis of Isopropyl 2-{[6-({N-[4-(1H-pyrazol-1-yl)benzyl]pyridine-3-sulfonamido}methyl)pyridin-2-yl]amino}acetate A glass vessel having an internal volume of about 50 ml and equipped with a stirrer, a thermometer and an upper cooling unit was loaded with 3.21 g (10.2 mmol) of N-[4-(1H-pyrazol-1-yl)benzyl]pyridine-3-sulfonamide, 2.43 g (10.0 mmol) of isopropyl 2-{[6-(chloromethyl)pyridin-2-yl]amino}acetate obtained in Example 6, 2.82 g (20.4 mmol) of potassium carbonate and 17.6 g of acetonitrile. The mixture was stirred while performing heating at 80° C. The reaction was performed for 10 hours until the area percentage of the raw material isopropyl 2-{[6-(chloromethyl)pyridin-2-ylamino]acetate in the high-performance liquid chromatography analysis fell to 0.03% or less. The reaction conversion of isopropyl 2-{[6-(chloromethyl)pyridin-2-yl]amino}acetate after 1 hour from the start of the thermal stirring was 43.9%. After the completion of the reaction, the reaction liquid was cooled to room temperature and was filtered through Celite (trade name), and the residue was washed with acetonitrile. The filtrate obtained was quantitatively analyzed by high-performance liquid chromatography, and was found to contain 5.00 g of the target product (96.0% reaction yield). Next, the reaction liquid was concentrated under reduced pressure until the weight of the liquid became 7.85 g. After the addition of 42.77 g of toluene, the product was washed with water three times. The resultant organic phase was combined with 31.5 ml (31.5 mmol) of 1 mol/L hydrochloric acid. The mixture was stirred at room temperature for 20 minutes and was separated. The separated organic phase contained 0.62 g of the target product (corresponding to 11.8% yield). To the aqueous phase were added 42.77 g of toluene and 34.6 ml (34.6 mmol) of a 1 mol/L aqueous sodium hydroxide solution. The mixture was heated to 40° C. and was stirred for 20 minutes. Hot filtration was performed at 40° C., and thereafter the liquid was separated. The organic phase obtained was washed with water two times. The organic phase was concentrated under reduced pressure until the weight of the liquid became 8.97 g, and 7.40 g of 2-propanol was added. The mixture was heated to 60° C., cooled gradually, and, at the temperature which caused a crystal to precipitate, stirred for 30 minutes. Thereafter, the mixture was cooled slowly to not more than 5° C., and stirred at the temperature for 1 hour. The resultant slurry was filtered, and the residue was washed with cold 2-propanol and vacuum dried at 50° C. to give 3.90 g of isopropyl 2-{[6-({N-[4-(1H-pyrazol-1-yl)benzyl]pyridine-3-sulfonamido}methyl)pyridin-2-yl]amino}acetate as a light brown solid (74.9% yield of isolation in terms of the raw material isopropyl 2-{[6-(chloromethyl)pyridin-2-yl]amino}acetate). The high-performance chromatography HPLC showed that the quantitative purity was 99.0% and the compound contained 0.11% of the raw material N-[4-(1H-pyrazol-1-yl)benzyl]pyridine-3-sulfonamide.

The properties of isopropyl 2-{[6-({N-[4-(1H-pyrazol-1-yl)benzyl]pyridine-3-sulfonamido}methyl)pyridin-2-yl]amino}acetate obtained are described below.

EI-MS (m/z): 520 [M].
CI-MS (m/z): 521 [M+1].
$^1$H-NMR (CDCl$_3$, δ (ppm)): 1.24 (6H, d, J=6.3 Hz), 3.82 (2H, d, J=5.5 Hz), 4.31 (2H, s), 4.64 (2H, s), 4.94 (1H, t, J=5.5 Hz), 5.07 (1H, sep, J=6.3 Hz), 6.26 (1H, d, J=8.3 Hz), 6.41 (1H, dd, J=7.2, 0.5 Hz), 6.46 (1H, dd, J=2.5, 1.8 Hz), 7.25 (1H, dd, J=8.3, 7.2 Hz), 7.32 (1H, ddd, J=8.0, 4.9, 0.8 Hz), 7.37-7.42 (2H, m), 7.62-7.66 (2H, m), 7.71 (1H, dd, J=1.8, 0.6 Hz), 7.93 (1H, dd, J=2.6, 0.6 Hz), 7.94 (1H, ddd, J=8.0, 2.4, 1.7 Hz), 8.69 (1H, dd, J=4.8, 1.6 Hz), 8.98 (1H, dd, J=2.4, 0.8 Hz).
$^{13}$C-NMR (CDCl$_3$, δ (ppm)): 21.8, 43.7, 51.0, 51.1, 68.9, 107.4, 107.7, 112.6, 119.2, 123.3, 126.7, 129.9, 133.8, 134.6, 137.3, 137.6, 139.8, 141.1, 148.0, 152.6, 153.2, 157.3, 170.5.
IR (KBr cm$^{-1}$): 764 (C—H), 1161 (S=O), 1525 (C=N), 1737 (C=O), (2981, 2933) (C—H), 3437 (N—H).
Elemental analysis: Calcd: C, 59.80%; H, 5.31%; N, 16.07%.
Found: C, 59.98%; H, 5.42%; N, 16.14%.

Comparative Example 1

Synthesis of Isopropyl 2-{[6-({N-[4-(1H-pyrazol-1-yl)benzyl]pyridine-3-sulfonamido}methyl)pyridin-2-yl]amino}acetate A glass vessel having an internal volume of about 50 ml and equipped with a stirrer, a thermometer and an upper cooling unit was loaded with 3.21 g (10.2 mmol) of N-[4-(1H-pyrazol-1-yl)benzyl]pyridine-3-sulfonamide, 2.43 g (10.0 mmol) of isopropyl 2-{[6-(chloromethyl)pyridin-2-yl]amino}acetate obtained in Example 6, 2.16 g (20.4 mmol) of sodium carbonate and 17.6 g of acetonitrile. The mixture was stirred while performing heating at 80° C. The reaction was performed for 110 hours until the area percentage of the raw material isopropyl 2-{[6-(chloromethyl)pyridin-2-yl]amino}acetate in the high-performance liquid chromatography analysis fell to 0.05% or less. The reaction conversion of isopropyl 2-{[6-(chloromethyl)pyridin-2-yl]amino}acetate after 1 hour from the start of the thermal stirring was 0.92%. After the completion of the reaction, the reaction liquid was cooled to room temperature and was filtered through Celite (trade name), and the residue was washed with acetonitrile. The filtrate obtained was quantitatively analyzed by high-performance liquid chromatography, and was found to contain 0.72 g of the target product (13.8% reaction yield). Next, the liquid was concentrated under reduced pressure until its weight became 7.85 g. After the addition of 42.6 g of toluene, the product was washed with water three times. Tar components which had separated during the washing with water were disposed of together with the aqueous phase. The resultant organic phase was combined with 31.5 ml (31.5 mmol) of 1 mol/L hydrochloric acid. The mixture was stirred at room temperature for 20 minutes and was separated. To the aqueous phase were added 42.6 g of toluene and 34.6 ml (34.6 mmol) of a 1 mol/L aqueous sodium hydroxide solution. The mixture was heated to 40° C. and was stirred for 20 minutes. Hot filtration was performed at 40° C., and thereafter the liquid was separated. The organic phase obtained was washed with water two times. The organic phase was concentrated under reduced pressure to give 0.764 of a dark brown viscous liquid containing isopropyl 2-{[6-({N-[4-(1H-pyrazol-1-yl)benzyl]pyridine-3-sulfonamido}methyl)pyridin-2-yl]amino}acetate. The high-performance chromatography HPLC showed that the quantitative purity was 60.2% and the net weight was 0.460 g (8.8% yield of isolation in terms of the raw material isopropyl 2-{[6-(chloromethyl)pyridin-2-yl]amino}acetate).

The properties of isopropyl 2-{[6-({N-[4-(1H-pyrazol-1-yl)benzyl]pyridine-3-sulfonamido}methyl)pyridin-2-yl]amino}acetate obtained are described below.

EI-MS (m/z): 520 [M].
CI-MS (m/z): 521 [M+1].
$^1$H-NMR (CDCl$_3$, δ (ppm)): 1.24 (6H, d, J=6.3 Hz), 3.82 (2H, d, J=5.5 Hz), 4.31 (2H, s), 4.64 (2H, s), 4.94 (1H, t, J=5.5 Hz), 5.07 (1H, sep, J=6.3 Hz), 6.26 (1H, d, J=8.3 Hz), 6.41 (1H, dd, J=7.2, 0.5 Hz), 6.46 (1H, dd, J=2.5, 1.8 Hz), 7.25 (1H, dd, J=8.3, 7.2 Hz), 7.32 (1H, ddd, J=8.0, 4.9, 0.8 Hz), 7.37-7.42 (2H, m), 7.62-7.66 (2H, m), 7.71 (1H, dd, J=1.8, 0.6 Hz), 7.93 (1H, dd, J=2.6, 0.6 Hz), 7.94 (1H, ddd, J=8.0, 2.4, 1.7 Hz), 8.69 (1H, dd, J=4.8, 1.6 Hz), 8.98 (1H, dd, J=2.4, 0.8 Hz).
$^{13}$C-NMR (CDCl$_3$, δ (ppm)): 21.8, 43.7, 51.0, 51.1, 68.9, 107.4, 107.7, 112.6, 119.2, 123.3, 126.7, 129.9, 133.8, 134.6, 137.3, 137.6, 139.8, 141.1, 148.0, 152.6, 153.2, 157.3, 170.5.
IR (KBr cm$^{-1}$): 764 (C—H), 1161 (S=O), 1525 (C=N), 1737 (C=O), (2981, 2933) (C—H), 3437 (N—H).

Example 5

Synthesis of Isopropyl 2-{[6-(hydroxymethyl)pyridin-2-yl]amino}acetate

A glass vessel having an internal volume of about 2 L and equipped with a stirrer, a thermometer and an upper cooling unit was loaded with 948 g of 2-propanol and 76.7 g of concentrated sulfuric acid. The mixture was heated to 75° C. There was added dropwise, over a period of 40 minutes, a mixed solution of 135 g of t-butyl 2-{[(t-butoxycarbonyl)(6-hydroxymethylpyridin-2-yl)]amino}acetate synthesized by the method described in Reference Example 3-(b) of Japanese Patent Application Publication No. 2011-57633, in 45 g of toluene and 311 g of 2-propanol. The resultant mixture was stirred for 6 hours while performing heating at 78° C. After being cooled, the liquid was vacuum concentrated at an internal pressure of 20 hPa and an external temperature of 40° C. until the weight of the liquid became 309 g. 677 g of toluene and 406 g of water were added, and the mixture was stirred at room temperature and was separated. The aqueous phase obtained was added dropwise, over a period of 20 minutes, to a separately prepared mixed solution of 129 g of sodium hydrogencarbonate in 812 g of water and 677 g of toluene. The resultant mixture was stirred at room temperature for 1 hour and was separated. The aqueous phase was extracted with 338 g of toluene. The organic phases obtained were combined and washed with 426 g of a 5 wt % aqueous sodium chloride solution. Thus, an organic phase weighing 1370 g was obtained. An approximately 1356 g portion was collected and concentrated until the weight of the liquid became 113 g. Thereafter, the weight of the liquid was adjusted to 300 g by the addition of toluene. To this solution, 190 g of n-heptane was added. The mixture was heated to 45° C. to dissolve the crystal and was thereafter cooled to 35° C. A small amount of a seed crystal synthesized separately by the similar process was added, and stirring was performed at 35° C. for 1 hour. The amount of the crystal increased gradually during the stirring. 365 g of n-heptane was added dropwise over a period of 30 minutes. The internal temperature was lowered to 5° C. in 40 minutes, and the mixture was stirred at the temperature for 30 minutes. The crystal precipitated was recovered by filtration, washed with n-heptane and dried at 50° C. under reduced pressure to give 70.4 g of isopropyl 2-{[6-(hydroxymethyl)pyridin-2-yl]amino}acetate as a white powder. The high-performance chromatography HPLC showed that the quantitative purity was 94.3% and the net weight was 66.4 g (74.7% yield of isolation in terms of the raw material t-butyl 2-{[(t-butoxycarbonyl)(6-hydroxymethylpyridin-2-yl)]amino}acetate).

The properties of isopropyl 2-{[6-(hydroxymethyl)pyridin-2-yl]amino}acetate obtained are described below.

EI-MS (m/z): 224 [M].
CI-MS (m/z): 225 [M+1].
$^1$H-NMR (CDCl$_3$, δ(ppm)): 1.27 (6H, d, J=6.3 Hz), 3.76 (1H, s), 4.10 (2H, d, J=5.5 Hz), 4.59 (2H, s), 5.00 (1H, s), 5.10 (1H, m), 6.36 (1H, dd, J=8.2, 0.6 Hz), 6.51 (1H, dd, J=7.3, 0.7 Hz), 7.41 (1H, ddd, J=5.74, 3.88 Hz).
$^{13}$C-NMR (CDCl$_3$, δ(ppm)): 21.8, 44.1, 63.5, 69.0, 106.6, 109.5, 138.0, 156.8, 156.9, 170.7.
IR (KBr cm$^{-1}$): 416, 469, 531, 559, 731, 785, 826, 862, 903, 916, 941, 980, 1014, 1052, 1082, 1106, 1131, 1147, 1182, 1217, 1256, 1276, 1347, 1378, 1402, 1471, 1526 (C=N), 1582, 1607, 1687, 1724 (C=O), 2878, 2935 (C—H), 2983 (C—H), 3381 (N—H).
Elemental analysis: Calcd: C, 58.91%; H, 7.19%; N, 12.49%.
Found: C, 58.99%; H, 7.17%; N, 12.48%.

Example 6

Synthesis of Isopropyl 2-{[6-(chloromethyl)pyridin-2-yl]amino}acetate

At room temperature, 19.6 g of thionyl chloride was added dropwise over a period of 20 minutes to a solution of 35.7 g of isopropyl 2-{[6-(hydroxymethyl)pyridin-2-yl]amino}acetate obtained in Example 5 in 396 g of methylene chloride. The mixture was stirred at room temperature for 1 hour. The resultant reaction liquid was added dropwise to a mixture slurry of 37.8 g of sodium hydrogencarbonate and 149 g of water. The mixture was stirred at room temperature for 20 minutes and was separated. The organic phase was dehydrated by the addition of 6.73 g of magnesium sulfate. The filtrate was concentrated to dryness at 50° C. In this manner, 37.8 g of isopropyl 2-{[6-(chloromethyl)pyridin-2-yl]amino}acetate was obtained as a light brown solid.

The properties of isopropyl 2-{[6-(chloromethyl)pyridin-2-yl]amino}acetate obtained are described below.

EI-MS (m/z): 242 [M].
CI-MS (m/z): 243 [M+1].
$^1$H-NMR (CDCl$_3$, δ (ppm)): 1.24 (6H, m), 4.10 (2H, d, J=5.4 Hz), 4.48 (2H, s), 5.03 (1H, s), 5.10 (1H, m), 6.39 (1H, d, J=8.3 Hz), 6.76 (1H, d, J=7.3 Hz), 7.43 (1H, dd, J=7.8, 7.8 Hz).
$^{13}$C-NMR (CDCl$_3$, δ (ppm)): 21.8, 44.0, 44.7, 68.9, 107.7, 112.2, 138.1, 154.6, 157.3, 170.7.
IR (KBr cm$^{-1}$): 415, 446, 530, 560, 627, 735, 804, 827, 874, 903, 939, 952, 982, 1042, 1088, 1108, 1128, 1144, 1167, 1180, 1219, 1269, 1281, 1350, 1378, 1400, 1420, 1434, 1470, 1525 (C=N), 1580, 1613, 1690, 1728 (C=O), 2878, 2934 (C—H), 2981 (C—H), 3379 (N—H).
Elemental analysis: Calcd: C, 54.44%; H, 6.23%; N, 11.54%.
Found: C, 54.46%; H, 6.23%; N, 11.56%.

INDUSTRIAL APPLICABILITY

The present invention relates to a method for obtaining an N-substituted sulfonamide compound with high purity by reacting a sulfonamide compound with a halogenated organic compound. The method for producing N-substituted sulfonamide compounds of the present invention involves a specific base, and thereby allows the reaction to proceed faster than heretofore possible and affords high yield with little byproducts, which makes the method of great usefulness in industry. Further, N-substituted sulfonamide compounds obtained by the method of the present invention have high purity and qualify for use as intermediates and active ingredients for drugs.

The invention claimed is:

1. A method for producing N-substituted sulfonamide compounds comprising a step of reacting a sulfonamide compound of the general formula (1):

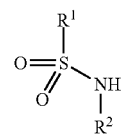

(1)

wherein
R$^1$ and R$^2$ are each independently an optionally substituted alkyl, alkenyl, alkynyl, cycloalkyl, aryl, heteroaryl, aralkyl or heteroarylalkyl group
with a halogenated organic compound of the general formula (2):

(2)

wherein
R³ is an optionally substituted aralkyl or heteroarylalkyl group, and X is a halogen atom
in the presence of cesium carbonate or potassium carbonate in an organic solvent to produce an N-substituted sulfonamide compound of the general formula (3):

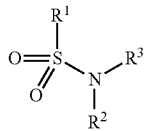
(3)

wherein R¹, R² and R³ are the same as defined above, wherein the halogenated organic compound of the general formula (2) is of the general formula (5):

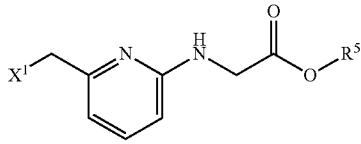
(5)

wherein R⁵ is an alkyl group, and X¹ is defined the same as X.

2. The method for producing N-substituted sulfonamide compounds according to claim 1, wherein R¹ is an optionally substituted aryl or heteroaryl group.

3. The method for producing N-substituted sulfonamide compounds according to claim 1, wherein R¹ is an optionally substituted phenyl or pyridyl group.

4. The method for producing N-substituted sulfonamide compounds according to claim 1, wherein R² is an optionally substituted aralkyl or heteroarylalkyl group.

5. The method for producing N-substituted sulfonamide compounds according to claim 1, wherein R² is an optionally substituted benzyl or benzofuranylmethyl group.

6. The method for producing N-substituted sulfonamide compounds according to claim 1, wherein X is a chlorine atom, a bromine atom or an iodine atom.

7. The method for producing N-substituted sulfonamide compounds according to claim 1, wherein X is a chlorine atom or a bromine atom.

8. The method for producing N-substituted sulfonamide compounds according to claim 1, wherein the sulfonamide compound of the general formula (1) is of the general formula (4):

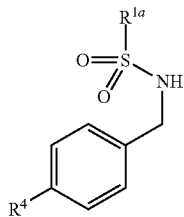
(4)

9. The method for producing N-substituted sulfonamide compounds according to claim 1, wherein the N-substituted sulfonamide compound of the general formula (3) is of the general formula (6):

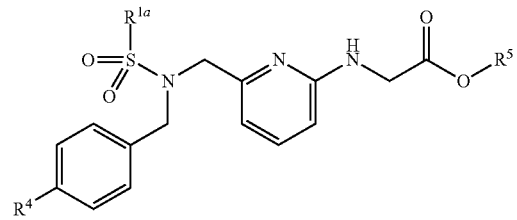
(6)

wherein R¹ᵃ, R⁴ and R⁵ are the same as defined above.

10. The method for producing N-substituted sulfonamide compounds according to claim 1, wherein the reaction temperature is 0 to 90° C.

11. The method for producing N-substituted sulfonamide compounds according to claim 1, wherein the organic solvent is one or more organic solvents selected from the group consisting of dimethylsulfoxide, dimethylformamide and acetonitrile.

12. The method for producing N-substituted sulfonamide compounds according to claim 1, wherein the organic solvent is acetonitrile.

13. A method for producing N-substituted sulfonamide compounds comprising a step of reacting a sulfonamide compound of the general formula (1):

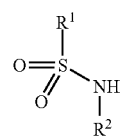
(1)

wherein
R¹ and R² are each independently an optionally substituted alkyl, alkenyl, alkynyl, cycloalkyl, aryl, heteroaryl, aralkyl or heteroarylalkyl group
with a halogenated organic compound of the general formula (2):

R³—X     (2)

wherein
R³ is an optionally substituted aralkyl or heteroarylalkyl group, and X is a halogen atom
in the presence of cesium carbonate in an organic solvent to produce an N-substituted sulfonamide compound of the general formula (3):

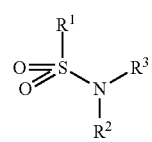
(3)

wherein R¹, R² and R³ are the same as defined above,
wherein the halogenated organic compound of the general formula (2) is of the general formula (5):

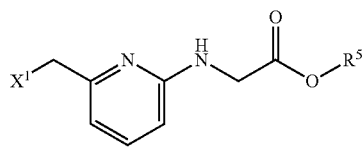
(5)
wherein $R^5$ is an alkyl group, and $X^1$ is defined the same as X.
14. The method for producing N-substituted sulfonamide compounds according to claim 13, wherein the reaction temperature is 30 to 90° C.
15. A compound of the general formula (9):
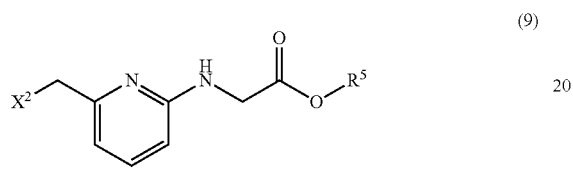
(9)
wherein $R^5$ is an alkyl group, and $X^2$ is a halogen atom or a hydroxyl group.
* * * * *